(12) United States Patent
Bittman et al.

(10) Patent No.: US 8,030,482 B2
(45) Date of Patent: Oct. 4, 2011

(54) FREE CHOLESTEROL ANALOGS BEARING A BORON DIPYRROMETHENE DIFLUORO (BODIPY) FLUOROPHORE IN THE SIDE CHAIN AND METHOD OF PREPARATION AND USE THEREOF

(75) Inventors: Robert Bittman, Roslyn Heights, NY (US); Zaiguo Li, Fresh Meadows, NY (US)

(73) Assignee: Research Foundation of the City University of New York, New York, NY (US)

( * ) Notice: Subject to any disclaimer, the term of this patent is extended or adjusted under 35 U.S.C. 154(b) by 812 days.

(21) Appl. No.: 12/013,120

(22) Filed: Jan. 11, 2008

(65) Prior Publication Data
US 2008/0177059 A1    Jul. 24, 2008

Related U.S. Application Data

(60) Provisional application No. 60/884,712, filed on Jan. 12, 2007.

(51) Int. Cl.
*C07J 43/00* (2006.01)
(52) U.S. Cl. .......................................................... 540/4
(58) Field of Classification Search ........................ 540/4
See application file for complete search history.

(56) References Cited

OTHER PUBLICATIONS

Shaw et al., "Correlated Fluorescence-Atomic Force Microscopy of Membrane Domains: Structure of Fluorescence Probes Determines Lipid Localization." Biophysical Journal, vol. 90, pp. 2170-2178, Mar. 2006.*
Li et al., "First Synthesis of Free Cholesterol—BODIPY Conjugates," *J. Org. Chem.*, 71, 1718-1721 (2006).
Shaw et al., "Correlated Fluorescence-Atomic Force Microscopy of Membrane Domains: Structure of Fluorescence Probes Determines Lipid Localization," *Biophysical Journal*, 90, 2170-2178 (2006).
Shaw, et al., "Tracking peptide-membrane interactions: Insights from in situ coupled confocal-atomic force microscopy imaging of NAP-22 peptide insertion and assembly," *Journal of Structural Biology*, 155, 458-469 (2006).

* cited by examiner

*Primary Examiner* — Barbara P Badio
(74) *Attorney, Agent, or Firm* — Hoffman & Baron, LLP

(57) ABSTRACT

The present invention relates to free cholesterol analogs bearing a boron dipyrromethene difluoro (BODIPY) fluorophore in the side chain and methods of preparation. The compounds of the present invention can be used in fluorescence spectroscopy and fluorescence microscopy to visualize the exchange, distribution, and trafficking of free cholesterol between living cells and to monitor the movement of free cholesterol between ordered and disordered lipid domains in membranes.

16 Claims, No Drawings

FREE CHOLESTEROL ANALOGS BEARING A BORON DIPYRROMETHENE DIFLUORO (BODIPY) FLUOROPHORE IN THE SIDE CHAIN AND METHOD OF PREPARATION AND USE THEREOF

This application asserts priority to U.S. Provisional Patent Application Ser. No. 60/884,712, filed Jan. 12, 2007, the contents of which are incorporated herein by reference.

BACKGROUND OF THE INVENTION

Unesterified (free) cholesterol is a major component of plasma membranes of eukaryotic cells and plays many roles in regulation of the biochemical and physiological properties of cells. Fluorescent spectroscopy and fluorescence microscopy have been frequently applied to study lipid-lipid and lipid-protein interactions in model membranes, cell membranes, and plasma lipoproteins.

Current fluorescent analogs of free cholesterol are inadequate. For example, analogs of unesterified cholesterol bearing a N,N-dimethylaminonaphthalenesulfonate (dansyl), pyrene, or a 7-nitrobenz-2-oxa-1,3-diazolyl-4-amino (NBD) moiety are not faithful mimics of free cholesterol as they are not capable of partitioning into liquid-ordered domains under conditions in which free cholesterol is known to partition into such domains. Thus, the existing fluorescent probes of free cholesterol are not adequate for studying the binding of free cholesterol to other lipids and to proteins and glycoproteins and for monitoring the dynamics of free cholesterol movement within membranes, cells, and lipoproteins.

As a result, new fluorescent analogs of free cholesterol are needed that mimic the physical behavior of free cholesterol in membranes and have desirable spectroscopic properties and physical properties for use in fluorescence studies with cells and model membranes. Likewise, new compounds are needed for examining whether the formation of membrane lipid domains (rafts) affect the physical and biochemical properties of cells.

SUMMARY OF THE INVENTION

In a first embodiment, the present invention is directed to free cholesterol analogs bearing a boron dipyrromethene difluoride (BODIPY) fluorophore having the formula I, II, or III,

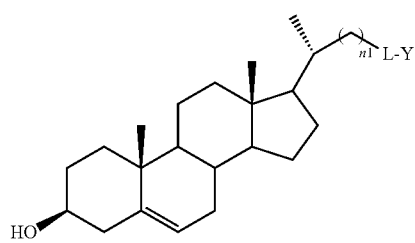

I

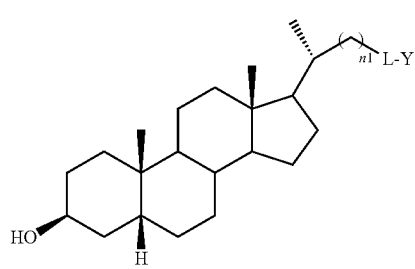

II

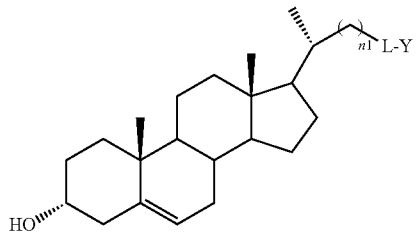

III wherein:

L represents a linker having one of the following structures:

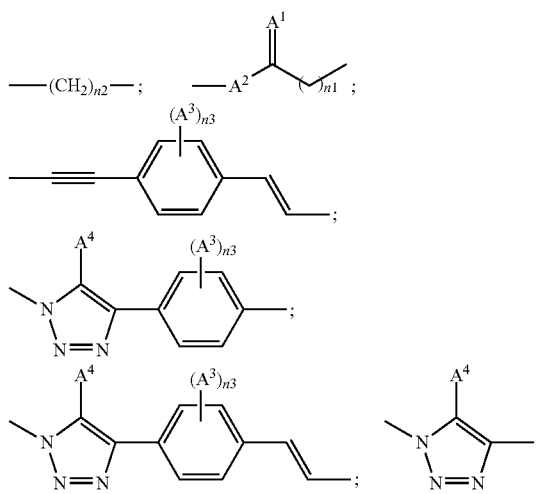

Y represents the following formula:

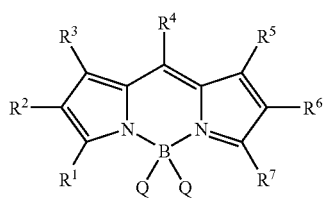

wherein:
- n1 is independently 1, 2, 3, 4, or 5;
- n2 is 0, 1, 2, 3, or 4;
- n3 is independently 0, 1, 2, 3, or 4;
- $A^1$ is O, S or $H_2$;
- $A^2$ is O, S, or NH;
- $A^3$ is independently alkyl, aryl, alkoxy, or aryloxy;
- $A^4$ is independently hydrogen, alkyl, or aryl;
- $R^1$, $R^2$, $R^3$, $R^4$, $R^5$, $R^6$, and $R^7$ independently represent hydrogen, alkyl, phenyl, alkoxy, or carboalkoxy; or $R^1$ and $R^2$, $R^2$ and $R^3$, $R^5$ and $R^6$, or $R^6$ and $R^7$ represent benzo provided that one of $R^1$ through $R^7$ represents a bond to L;
- Q is fluoro, alkyl, alkoxy, or aryloxy;
- alkyl groups are unbranched, saturated, and have 1-4 carbon atoms;
- aryl groups can be either carbocyclic aryl or heterocyclic aryl;

carbocyclic aryl groups have a total of 6-20 carbon atoms, including carbon atoms of substituents;
heterocyclic aryl groups have a total of 5-20 carbon atoms, including carbon atoms of substituents;
alkoxy groups are alkyloxy groups wherein alkyl groups are as defined above;
the aryl groups of aryloxy are as described above;
carboalkoxy groups are alkyl esters of a carboxylic acid wherein alkyl groups are as defined above;
each alkyl, aryl, alkoxy, aryloxy, benzo, and carboalkoxy, independently, may be unsubstituted or substituted with one or more substituent;
alkyl substituents are halo, hydroxyl, amino, or aryl;
aryl substituents are halo, hydroxyl, amino, alkyl, aryl, nitro, or carboxyl; and
halo substituents are fluoro or chloro.

In a second embodiment, the invention is directed to a molecule according to the first embodiment having formula I or II.

In a third embodiment, the invention is directed to a molecule according to the first embodiment wherein:
n1 is independently 1 or 2;
n2 is 0 or 1;
n3 is 0;
$A^1$ is O;
$A^2$ is O;
$A^4$ is hydrogen;
Q is fluoro;
$R^1$, $R^2$, $R^3$, $R^4$, $R^5$, $R^6$, and $R^7$ independently represent hydrogen or alkyl;
alkyl groups are methyl and ethyl; and
aryl groups are phenyl.

In a fourth embodiment, the invention is directed to a molecule according to the first embodiment having formula I or II wherein:
L represents

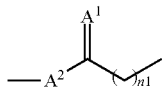

$R^4$ represents a bond to L; and
Q is fluoro.

In a fifth embodiment, the invention is directed to a molecule according to the fourth embodiment, having formula I.

In a sixth embodiment, the invention is directed to a molecule according to the first embodiment having formula I or II wherein:
L represents

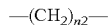

n2 is 0;
$R^4$ represents a bond to L; and
Q is fluoro.

In a seventh embodiment, the invention is directed to a molecule according to the fourth embodiment, having formula I.

In a eighth embodiment, the invention is directed to a molecule according to the first embodiment having formula I or II wherein:
L represents

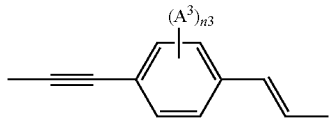

n3 is 0;
$R^1$ represents a bond to L; and
Q is fluoro.

In a ninth embodiment, the invention is directed to a molecule according to the fourth embodiment, having formula I.

In a tenth embodiment, the invention is directed to a molecule according to the first embodiment having formula I or II wherein:
L represents

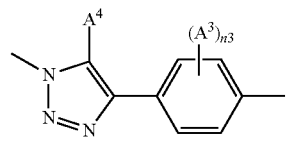

$A^4$ is hydrogen;
n3 is 0;
$R^4$ represents a bond to L; and
Q is fluoro.

In an eleventh embodiment, the invention is directed to a molecule according to the fourth embodiment, having formula I.

In a twelfth embodiment, the invention is directed to a molecule according to the first embodiment having formula I or II wherein:
L represents

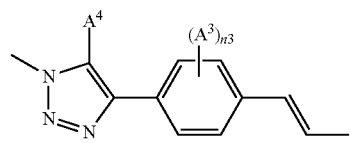

$A^4$ is hydrogen;
n3 is 0;
$R^1$ represents a bond to L; and
Q is fluoro.

In a thirteenth embodiment, the invention is directed to a molecule according to the fourth embodiment, having formula I.

In an fourteenth embodiment, the invention is directed to a molecule according to the first embodiment having formula II wherein:
L represents

n2 is 0;
$R^4$ represents a bond to L; and
Q is fluoro.

In a fifteenth embodiment, the invention is directed to a molecule according to the first embodiment having formula I or II wherein:
L represents

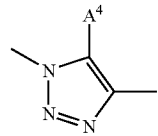

$A^4$ is hydrogen;
$R^2$ represents a bond to L; and
Q is fluoro.

In a sixteenth embodiment, the invention is directed to a molecule according to the fourth embodiment, having formula I.

DETAILED DESCRIPTION OF THE INVENTION

It has now been discovered that free cholesterol analogs bearing a boron dipyrromethene difluoride (BODIPY) fluorophore in the side chain mimic the physical behavior of free cholesterol in membranes and have desired spectroscopic properties and physical properties for use in fluorescence studies with cells, lipoproteins, and model membranes. Additionally, fluorescent analogs of sterol 5β-cholestan-3β-ol (coprostanol) are useful for examining whether the formation of membrane lipid domains (rafts) affect the physical and biochemical properties of cells and for examining sterol dynamics in the non-raft domains of membranes of living cells.

The present invention is directed to free cholesterol analogs bearing a BODIPY fluorophore and coprostanol analogs bearing a BODIPY fluorophore. The compounds have the formula I, II, or III:

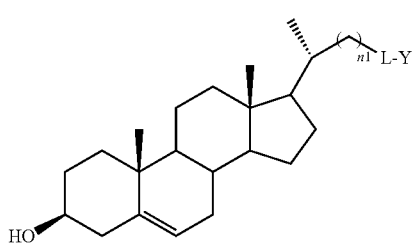

I

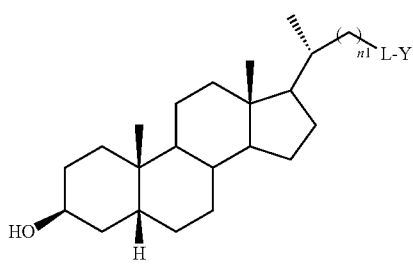

II

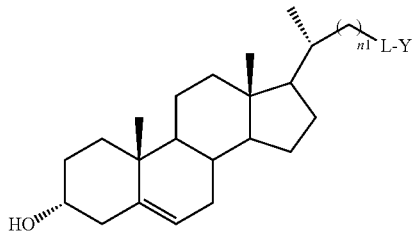

III

In a preferred embodiment, the compounds have the formula I or II.

The compounds of formula I represent free cholesterol analogs, whereas the compounds of formula II represent coprostanol analogs. The compounds of formula III represent free cholesterol analogs in which the configuration at C-3 is inverted, i.e., 3α-hydroxy, instead of the naturally occurring 3β-hydroxy configuration shown in formulas I and II.

In the above formulas, L represents a linker having one of the following structures:

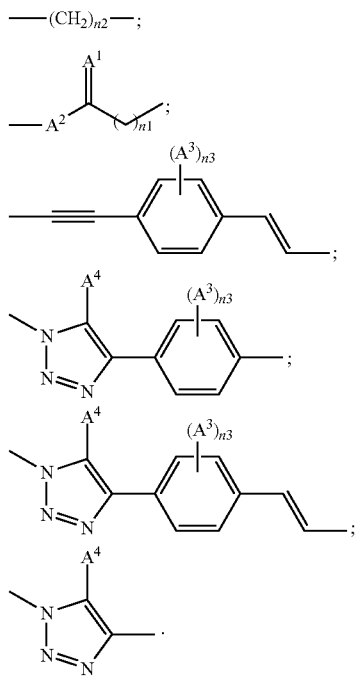

Y represents a BODIPY having the following formula:

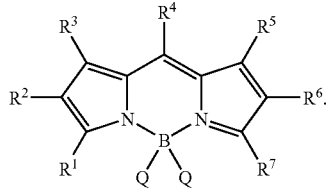

The letter n1 independently represents 1, 2, 3, 4, or 5. For example, the molecule may comprise formula I wherein n1 is 2 and L may represent

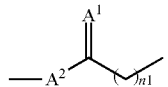

wherein n1 is 4.

The letter n2 represents 0, 1, 2, 3, or 4. For example, when the linker L is:

wherein n2 is 4, the linker is a $C_4$ hydrocarbon chain.

The symbol n3 is 0, 1, 2, 3, or 4. For example, the linker may be represented by

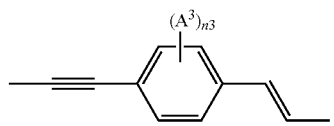

wherein n3 is 0. In this example, the aryl structure contains no $A^3$ substituents.

In the linker represented by the following structure

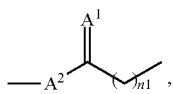

$A^1$ is O, S, or $H_2$ and $A^2$ is O, S, or NH. For example, when $A^1$ and $A^2$ are O, the linker is an ester. When $A^1$ is $H_2$, the linker contains a methylene group.

$A^3$ is independently alkyl, aryl, alkoxy, or aryloxy. $A^4$ is independently hydrogen, alkyl, or aryl.

$R^1$, $R^2$, $R^3$, $R^4$, $R^5$, $R^6$, and $R^7$ independently represent hydrogen, alkyl, phenyl, alkoxy, or carboalkoxy; or $R^1$ and $R^2$, $R^2$ and $R^3$, $R^5$ and $R^6$, or $R^6$ and $R^7$ represent benzo provided that one of $R^1$ through $R^7$ represents a bond to L. For example, when $R^1$, $R^3$, and $R^5$ are methyl; $R^6$ and $R^7$ are benzo; and $R^4$ represents a bond to L, the following structure results:

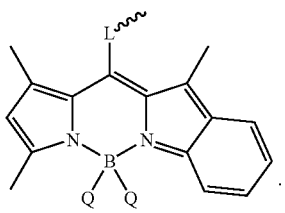

Q is fluoro, alkyl, alkoxy, and aryloxy. In a preferred embodiment, Q is fluoro.

Alkyl groups are unbranched, saturated, and have 1-4 carbon atoms. Examples of alkyl groups include methyl, ethyl, propyl, and butyl.

Aryl groups can be either carbocyclic aryl or heterocyclic aryl. Carbocyclic aryl groups contain a minimum of six carbon atoms. The maximum number of carbon atoms is twenty, including carbon atoms, if any, of optional substituents and/or fused rings.

Heterocyclic aryl groups contain a minimum of five carbons. The maximum number of carbon atoms is twenty carbon atoms, including carbon atoms, if any, of optional substituents and/or fused rings.

Carbocyclic aryl groups can be unfused or fused. A preferred unfused carbocyclic aryl group is phenyl. Some examples of other fused carbocyclic aryl groups include naphthyl, phenanthryl, and anthracenyl.

Heterocyclic aryl groups contain one or more ring heteroatoms, e.g., nitrogen, oxygen, or sulfur atoms, and may be unfused or fused. Some examples of unfused heterocyclic aryl groups include thiophenyl, furyl, and pyrrolyl. Some examples of fused heterocyclic aryl groups include purinyl, indolyl, benzofuranyl, and benzopyranyl.

Alkoxy groups are alkyloxy groups wherein alkyl groups are as defined above. Examples of alkoxy groups include methoxy, ethoxy, propoxy, and butoxy.

Aryloxy groups contain aryl groups as described above. A preferred aryloxy is phenoxy. Some examples of other aryloxy groups include naphthyloxy, pyrenyloxy, and furyloxy.

Carboalkoxy groups are alkyl esters of a carboxylic acid wherein alkyl groups are as defined above. Examples of carboalkoxy groups include carbomethoxy, carboethoxy, carbopropoxy, and carbobutoxy.

Each alkyl, aryl, alkoxy, aryloxy, benzo, and carboalkoxy, independently, may be unsubstituted or substituted with one or more substituent. Alkyl substituents are halo, hydroxyl, amino, or aryl. Aryl substituents are halo, hydroxyl, amino, alkyl, aryl, nitro, or carboxyl. Halo substituents are fluoro and chloro. Alkyl and aryl are as defined above.

In the present invention, various parameters are defined (e.g. L, $A^1$, $A^2$, n1, Y). Within each parameter, more than one element (e.g. number, chemical moieties) are listed. It is to be understood that the instant invention contemplates embodiments in which each element listed under one parameter, may be combined with each and every element listed under any other parameter. For example, $A^1$ is identified above as representing O, S or $H_2$. $A^2$ is identified above as being O, S, or NH. Each element of $A^1$ (O, S or $H_2$) can be combined with each and every element of $A^2$ (O, S, or NH). For example, in one embodiment, $A^1$ may be O and $A^2$ may be O. Alternatively, $A^1$ may be $H_2$ and $A^2$ may be S, etc. Similarly, a third parameter is n1, in which the elements are defined as 0, 1, 2, 3, 4, or 5. Each of the above embodiments may be combined with each and every element of n1. For example, in the embodiment wherein $A^1$ is O and $A^2$ is O, n1 may be 2 (or any other number within the elements of n1).

Uses of the Compounds

The compounds of the present invention have numerous uses. Some of the uses involve the detection and investigation of lipid rafts in living cells and in model membranes. Free cholesterol is known to be an essential component of membrane domains known as membrane lipid raft domains. Lipid rafts are implicated in signal transduction events.

Compounds of structure B below possess the physical properties required for cholesterol to enter into lipid rafts, as assayed by detergent insolubility measurements and atomic force microscopy. Compounds of structure A below do not possess such physical properties, as assayed by detergent insolubility measurements and atomic force microscopy; therefore, they represent the desired property of acting as a negative control and are also useful for assessing sterol dynamics in the non-raft domains of membranes. See J. E. Shaw, R. F. Epand, R. M. Epand, Z. Li, R. Bittman, and C. M. Yip, "Correlated Fluorescence-AFM Microscopy of Membrane Domains: Structure of Fluorescence Probes Determines Lipid Localization," Biophys. J. 90, 2170-2178 (2006) and J. E. Shaw, R. F. Epand, K. Sinnathamby, Z. Li, R. Bittman, R. M. Epand, and C. M. Yip, "Tracking Peptide-Membrane Interactions: Insights from in situ Coupled Confocal-Atomic Force Microscopy Imaging of NAP-22 Peptide Insertion and Assembly," J. Struct. Biol. 155, 458-469 (2006).

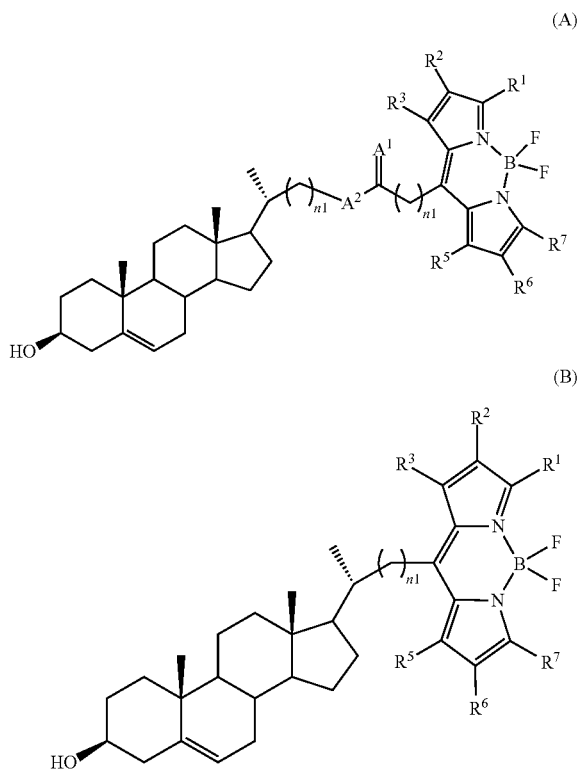

(A)

(B)

Compounds of this invention are readily delivered to the plasma membrane of cells as solutions in alcohol or polar organic solvents, or as a complex with water-soluble cyclodextrins, or as a complex with defatted serum albumin in aqueous buffer, or as an aqueous suspension in bilayer membranes (liposomes or vesicles prepared with phospholipids such as phosphatidylcholine or sphingomyelin). In another embodiment, the compounds of the invention are delivered to the plasma membrane as a complex in growth medium containing lipoprotein-deficient serum. The compounds of the invention can be used to visualize membrane domains and to screen for new drug candidates or other agents that disrupt the formation of membrane lipid rafts and thereby interfere with normal intracellular cell signaling cascades.

Another use of the claimed compounds involves monitoring the trafficking of free cholesterol along the endocytic pathway of cultured mammalian cells by fluorescence microscopy. The excimer-forming spectral properties and photostability of the fluorophore in compounds A-G above and below permit an estimation of the relative concentrations of free cholesterol in intracellular compartments. Agents that may disrupt the abnormal accumulation of free cholesterol in diseased cells, such as in various lipid-storage disorders such as Niemann-Pick disease, can be readily screened by using compounds of structures A, B, and D-G.

The compounds in the invention permit the study of the interactions of free cholesterol with other lipids (such as phosphatidylcholine and sphingomyelin) and with (glyco) proteins during endocytosis and exocytosis. An improved understanding of these pathways is important since these pathways are utilized for delivery of many bacterial toxins, bacteria, and viruses.

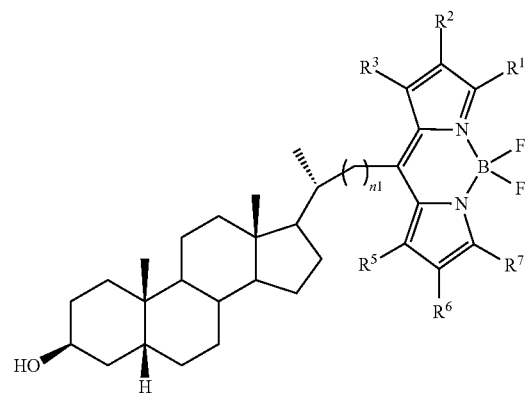

(C)

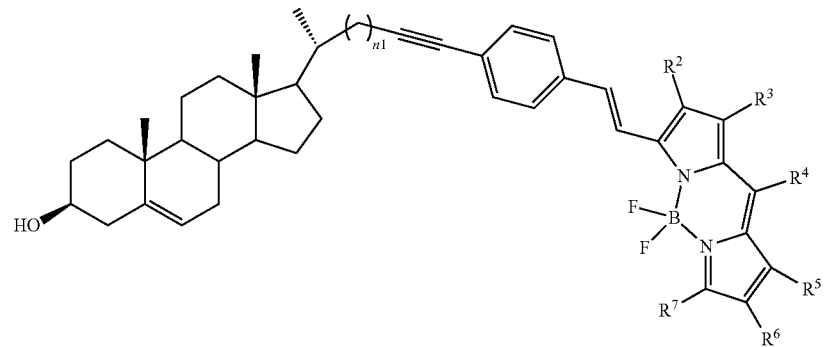

(D)

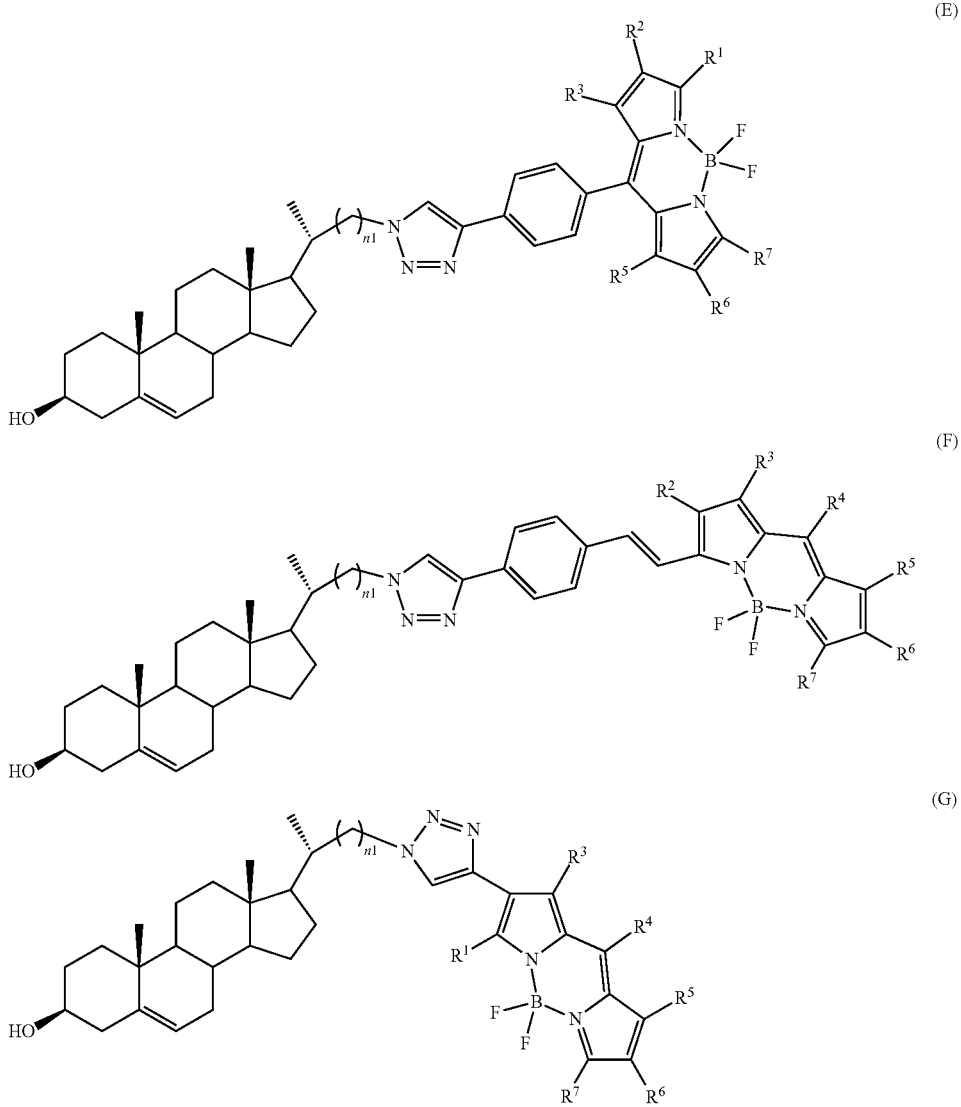

In yet another application, the compounds of the present invention can be used as a substitute for radiolabeled free cholesterol in studies of cholesterol metabolism in cells and plasma lipoproteins. Compounds of structures A and B were incorporated into the surface of reconstituted lipoprotein particles. When the reconstituted lipoproteins that were loaded with compounds of structures A and B were incubated with human embryonic fibroblast cells in tissue culture, the compounds of structures A and B were readily taken up by the cells as detected by cellular fluorescence. Compounds of structures A and B were efficiently esterified intracellularly by acyl-CoA:cholesterol O-acyltransferase (ACAT), a key enzyme in atheroma foam cell formation, in Fu5AH and J774 macrophages to form the corresponding fluorescent cholesteryl ester product. The esterification of compounds of structures A and B was blocked when an inhibitor of ACAT was added, indicating that compounds of structures A and B mimic the behavior of tritiated and carbon-14 labeled free cholesterol with respect to esterification in tissue culture. As a result, these compounds can be used to screen for specific inhibitors of ACAT enzymes that are responsible for the formation of cholesteryl esters in tissues. Compounds in this invention allow the fluorescence monitoring of free cholesterol efflux from macrophages and other cells, including vascular cells, and the transport of free cholesterol between lipoproteins, between cells and serum components, and between cells and lipid-free apolipoproteins or other extracellular acceptors.

Analysis by fluorescence rather than by radioactivity counting methods offers the advantage of high sensitivity without incurring the problems associated with disposal and safety in the handling of radiolabeled materials. The compounds of this invention will provide a tool for screening cells that have mutations in aspects of cholesterol metabolism without the need to use radiolabeled cholesterol. For example, fluorescence activated cell sorting will indicate cell populations that retain and accumulate the fluorescent sterol because of a defect in the cholesterol efflux pathway; conversely, cells that contain low levels of fluorescence will be tested for enhanced levels of cholesterol efflux.

The compounds of this invention also serve as a model substrate of lecithin-cholesterol acyltransferase (LCAT).

LCAT is the major enzyme involved in the esterification of free cholesterol in plasma lipoproteins and is a determinant of plasma high-density lipoprotein concentrations. Compounds of this invention will be used to screen for inhibitors and activators of LCAT, in place of the commonly used radioactive forms of free cholesterol as the substrate. The oxidation of cholesterol to form oxidized products, such as 7-hydroxy-, 7-keto-, and 25-hydroxycholesterol, is also usually monitored by using radioactive cholesterol as a tracer; however, the compounds of this invention permit fluorescence to be employed as an alternative method to assay the oxidation of free cholesterol, again eliminating the need for using radioactive cholesterol as the substrate of LCAT and oxidizing conditions.

Additionally, the compounds are useful as a substitute for radiolabeled free cholesterol to study the rates and extent of exchange of free cholesterol between cells and to directly study the binding of free cholesterol with various proteins and other lipids that regulate the intracellular movement of cholesterol.

An additional use of the compounds is as a fluorogenic probe to monitor lipid oxidation induced by peroxyl, hydroxyl, and alkoxyl radicals, peroxynitrite, superoxide radical anion, and other reactive oxygen species. Free cholesterol analogs bearing the BODIPY fluorophore are readily incorporated into model bilayer membranes (liposomes), together with free cholesterol, phosphatidylcholine, and sphingomyelin. On exposure of liposomes containing 1 mol percent of BODIPY-cholesterol to free radical initiators, the fluorescence intensity of the probe is markedly decreased at wavelengths where naturally occurring biological molecules do not exhibit fluorescence. The compounds of this invention can be used to conveniently screen for lipophilic compounds that possess antioxidant activity and thereby inhibit the oxidation of membrane lipids, as measured by the retention of the fluorescence intensity of BODIPY-cholesterol.

Synthesis of the Compounds

The syntheses of compounds of structure A involved the preparation and coupling of structures H and I.

Structure H represents a series of free cholesterol analogs with an aliphatic side chain of varying length (designated by n1 in structure H), a protected 3β-hydroxy group (designated as P in structure H), and a functional group in the side chain (designated as X in structure H, wherein X is OH, SH, or $NH_2$).

Structure I represents BODIPY analogs in which there are bathochromic moieties $R^1$ to $R^6$ on the ring system and functional groups $A^1$ and $A^2$ (wherein $A^1$ is O, S or $H_2$ and $A^2$ is OH, p-nitrophenoxy, succinimidyl, or halogen) on the side chain attached to the central methylene carbon via a linker of variable length (n1 methylene groups).

Compounds of structure A were obtained by coupling of compound H with compound I, followed by deprotection of the 3β-hydroxy group. Compounds of structure I (wherein $A^1$ is O, S, or $H_2$; $A^2$ is OH, p-nitrophenoxy, succinimidyl, or halogen) were synthesized by the reaction of two equivalents of a substituted pyrrole with the corresponding acyl chloride or with a cyclic anhydride followed by chelation with boron trifluoroetherate ($BF_3.OEt_2$) in the presence of an organic base such as triethylamine ($Et_3N$). See Z. Li, E. Mintzer, and R. Bittman, "First Synthesis of Free Cholesterol—BODIPY Conjugates," J. Org. Chem. 71, 1718-1721 (2006).

Compounds of structure B are synthesized by using a cholesterol analog of structure J, which bears a 3β-acetate group and a carboxylic acid group (G=OH) in the side chain. Reaction of carboxylic acid J with oxalyl chloride or thionyl chloride yields the acyl chloride of compound J (G=Cl).

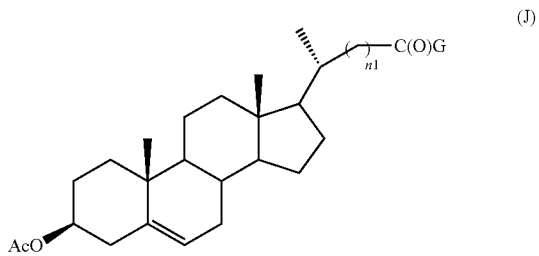

(J)

Compounds of structure B were obtained by the following reaction sequence: (a) condensation of the acyl chloride of compound J with substituted pyrroles in dichloromethane under reflux, (b) a chelation reaction with boron trifluoroetherate ($BF_3.OEt_2$) in the presence of an organic base, and (c) hydrolysis of the 3β-acetate group with potassium carbonate or sodium carbonate in methanol, ethanol, or a mixture of solvents, such as a methanol/dichloromethane mixture.

Coprostanol analogs bearing a 3β-acetate group and a carboxylic acid group in the side chain (structure K below) were used to synthesize the compounds of structure C by methods similar to those used to synthesize compound B. Compound C (wherein n1=2, $R^2$=$R^4$=$R^5$=$R^6$=$CH_3$, $R^3$=$R^6$=H), was prepared by converting the 3α-hydroxy group of lithocholic acid into a 3β-acetate group. For example, lithocholic acid is reacted with methanesulfonyl chloride to form the corresponding mesylate. This reaction is followed by inversion by treatment with cesium acetate in toluene at reflux in the presence of a crown ether (18-crown-6). The carboxyl group of the resulting compound is then converted to the acyl chloride with oxalyl chloride or thionyl chloride, and the condensation reaction with the substituted pyrrole affords the BODIPY fluorophore as described above in the synthesis of compounds of structure B. The acetyl group was removed by base-catalyzed hydrolysis.

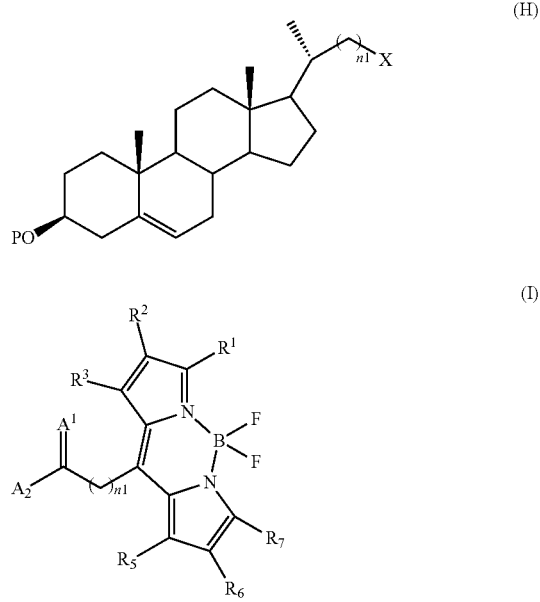

(H)

(I)

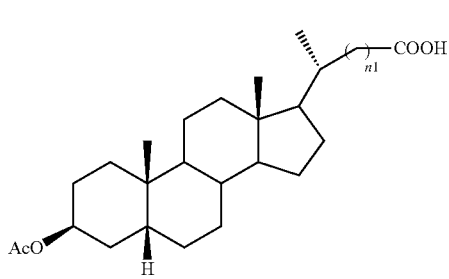

(K)

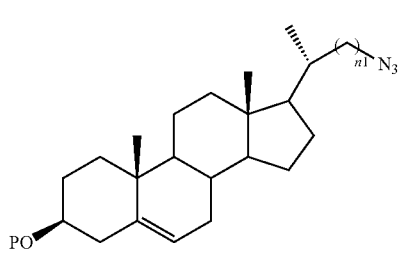

(N)

Compounds of structure D were synthesized from two fragments: structures L and M.

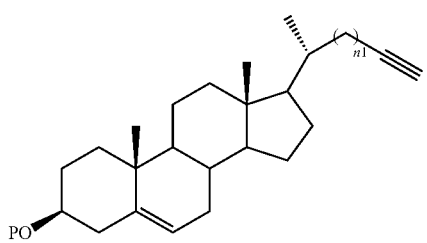

(L)

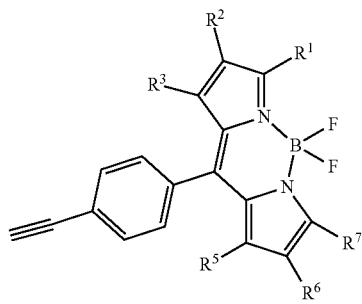

(O)

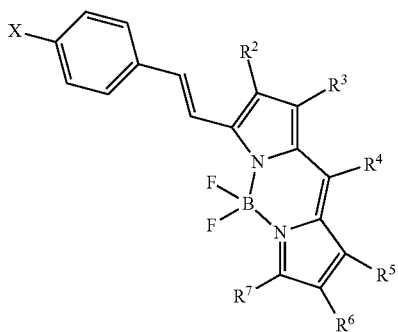

(M)

Compounds of structure F were synthesized by a similar cycloaddition reaction of azide N with alkyne M (wherein X=—C≡CH), which was made from substituted 2-(4-ethynylphenylvinyl)pyrrole.

Compounds of structure G are synthesized by a similar cycloaddition reaction of azide N with alkyne P (wherein X=—C≡CH), which is made from the corresponding halide P (wherein X=halogen), followed by deprotection of the 3β-hydroxyl group.

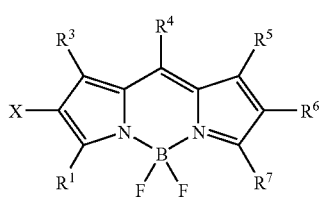

(P)

Compounds of structure L were prepared by alkynylation of the corresponding halide. The halide was obtained by reduction of the corresponding carboxylic acid with lithium aluminum hydride, followed by conversion of the resulting hydroxy group to halide by standard methods such as mesylation with methanesulfonyl chloride and substitution with a lithium halide or sodium halide. Alkynylation was accomplished by reaction of the halide with lithium acetylide ethylenediamine complex in dimethyl sulfoxide at low temperature. Compounds of structure M were synthesized from (substituted) 2-phenylvinyl-pyrroles, which were obtained by the Wittig reaction of (substituted) 2-formyl-pyrrole. The coupling of L and M was achieved in the presence of a transition metal catalyst to provide compounds of structure D.

Compounds of structure E were synthesized by a 1,3-dipolar cycloaddition reaction of (protected) azide N with alkyne O in the presence of a cuprous or ruthenium(II) ion catalyst. Compounds of structure N were obtained by substitution of the halide by treatment with sodium azide or lithium azide. Compounds of structure O were prepared from p-ethynylbenzaldehyde with two equivalents of the pyrrole compound.

The synthesis of compound III involves the conversion of the 3β-hydroxy group in compound I to a 3α-hydroxy group. The inversion of configuration at C-3 was achieved by a Mitsunobu reaction of compound I with chloroacetic acid, diisopropyl azodicarboxylate, and triphenylphosphine. The resulting α-chloroacetate intermediate was hydrolyzed readily with a weak base (such as potassium carbonate, sodium carbonate) in methanol or ethanol to provide compound III.

EXAMPLES

Examples have been set forth below for the purposes of illustration and to describe the best mode of the invention at the present time. The scope of the invention is not to be in any way limited by the examples set forth herein.

Example 1

Synthesis of 3β-tetrahydropyranyloxy-23-bisnor-chol-5-en-22-ol (compound 1)

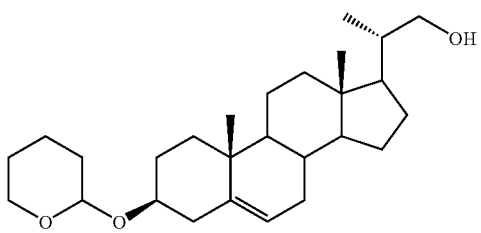

To a solution of 44 mg (0.13 mmol) of bisnorcholenic acid in 5 mL of dry tetrahydrofuran (THF) were added 55 mg (0.65 mmol) of 3,4-dihydro-2H-pyran (DHP) and 5 mg (0.026 mmol) of p-toluenesulfonic acid monohydrate (p-TsOH) under nitrogen. After the mixture was stirred at room temperature for 24 h, saturated aqueous NaHCO₃ solution (5 mL) and dichloromethane (CH₂Cl₂) (10 mL) were added. The aqueous layer was extracted with CH₂Cl₂ (2×10 mL), the combined organic layers were acidified with acetic acid (3 mL), washed with water (3×10 mL), and dried (Na₂SO₄). The solvent was removed under vacuum, and the crude carboxylic acid was used without further purification. A solution of the crude acid in 5 mL of dry THF was added dropwise to a suspension of lithium aluminum hydride (LiAlH₄) (4.9 mg, 0.13 mmol) in dry THF (3 mL) under nitrogen at 0° C. After the addition, the reaction mixture was allowed to warm to room temperature and stirred overnight. Saturated aqueous NaHCO₃ solution (5 mL) was added carefully, and the resulting mixture was extracted with CH₂Cl₂ (3×10 mL). The combined organic layers were washed with saturated aqueous NaCl solution (2×15 mL) and dried (Na₂SO₄). The solvent was removed, and the residue was purified by chromatography on silica gel (elution with hexane/ethyl acetate 4:1) to give 42 mg (79%) of compound 1 as a white solid.

Example 2

Synthesis of 4-(4,4-difluoro-1,3,5,7-tetramethyl-4-bora-3a,4a-diaza-s-indacene-8-yl)-butyric Acid (Compound 2)

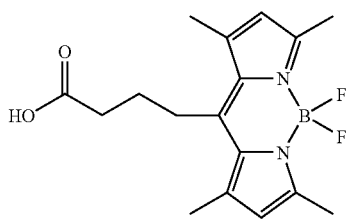

To a nitrogen-flushed round-bottom flask were added consecutively glutaric anhydride (68 mg, 0.60 mmol), dry CH₂Cl₂ (10 mL), 2,4-dimethylpyrrole (112 mg, 1.20 mmol), and BF₃.OEt₂ (0.11 g, 0.80 mmol). The mixture was heated at reflux for 5 h. After the mixture was cooled to room temperature, BF₃.OEt₂ (0.56 g, 4.0 mmol) and Et₃N (0.30 g, 3.0 mmol) were added. The reaction mixture was stirred under nitrogen at room temperature overnight, and then washed with water (2×10 mL). The organic phase was dried (Na₂SO₄), and the solvent was evaporated under vacuum. The resulting dark oil was purified by chromatography on silica gel (elution with hexane/ethyl acetate 2:1) to give 32 mg (16%) of BODIPY-butyric acid compound 2 as a dark red solid.

Example 3

Synthesis of 3β-tetrahydropyranyloxy-22-[4-(4,4-difluoro-1,3,5,7-tetramethyl-4-bora-3a,4a-diaza-s-indacene-8-yl)butyroxy]-23-bisnorchol-5-ene (Compound 3)

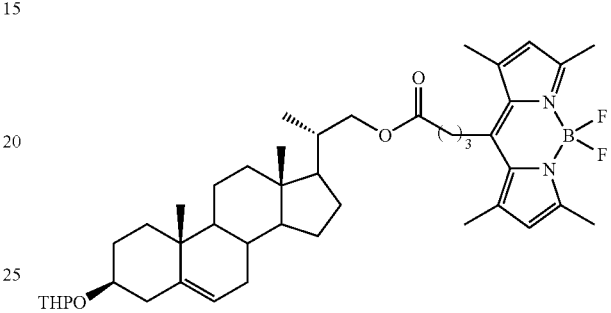

To a solution of 14.1 mg (44.1 μmol) of compound 1 and 18.3 mg (44.1 μmol) of compound 2 in 5 mL of dry CH₂Cl₂ were added 13.6 mg (66.2 μmol) of dicyclohexylcarbodiimide (DCC) and 2 mg (17 μmol) of 4-dimethylaminopyridine (DMAP) under nitrogen. After the mixture was stirred at room temperature for 1 day, water (3 mL) was added and the organic phase was separated and dried (Na₂SO₄). The solvent was removed under vacuum, and the residue was purified by chromatography on silica gel (elution with hexane/ethyl acetate 8:1) to give 24 mg (73%) of compound 3 as a dark red solid.

Example 4

Synthesis of 22-[4-(4,4-difluoro-1,3,5,7-tetramethyl-4-bora-3a,4a-diaza-s-indacen-8-yl)butyroxy]-23,24-bisnorchol-5-en-3β-ol (Compound 4, structure I, wherein n=1, m=3, X=Y=O, $R^1=R^3=R^4=R^6=CH_3$, $R^2=R^5=H$)

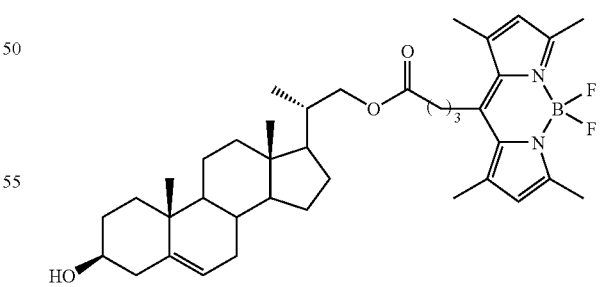

A solution of compound 3 (13.1 mg, 17.8 μmol) and p-pyridinium toluenesulfonate (PPTS) (5 mg, 19.9 μmol) in methanol (5 mL) was heated at 55° C. until the reaction was complete (~3 h, monitored by TLC using hexane/ethyl acetate, 4:1). After the solvent was removed under vacuum, 11 mg (92%) of compound 4 was obtained by chromatography on silica gel (elution with hexane/ethyl acetate, 4:1).

Example 5

Synthesis of 3β-acetoxy-23-(4,4-difluoro-1,3,5,7-tetramethyl-4-bora-3a,4a-diaza-s-indacene-8-yl)-24-norchol-5-ene (Compound 5)

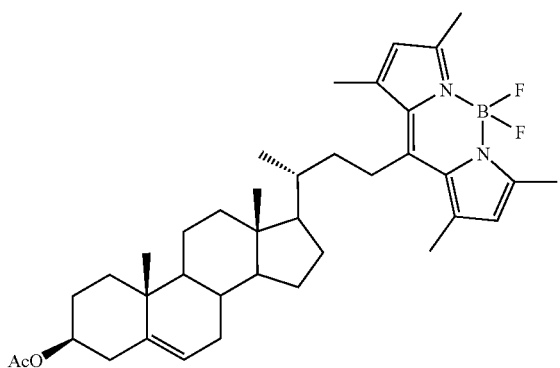

To a solution of 100 mg (0.24 mmol) of cholenic acid 3β-acetate in 10 mL of dry $CH_2Cl_2$ was added 121 mg (0.96 mmol) of oxalyl chloride under nitrogen at 0° C. After the mixture had warmed to room temperature overnight with stirring, the volatiles were removed under high vacuum to give crude acyl chloride as a white solid, which was dissolved in dry $CH_2Cl_2$ (10 mL). After 2,4-dimethylpyrrole (50.4 mg, 0.53 mmol) was added, the reaction mixture was heated at reflux for 4 h under nitrogen, and then cooled to room temperature. $BF_3.OEt_2$ (200 mg, 1.44 mmol) and triethylamine ($Et_3N$) (100 mg, 0.96 mmol) were added, and the mixture was stirred overnight under nitrogen. Water (10 mL) was added, and the organic phase was separated and dried ($Na_2SO_4$). After the solvent was evaporated, the residue was purified by chromatography on silica gel (elution with hexane/ethyl acetate 8:1) to give 43 mg (29%) of compound 5 as a dark red solid.

Example 6

Synthesis of 23-(4,4-difluoro-1,3,5,7-tetramethyl-4-bora-3a,4a-diaza-s-indacen-8-yl)-24-norchol-5-en-3β-ol (Compound 6)

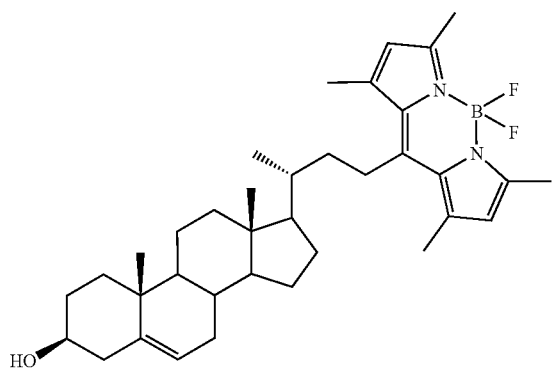

A mixture of compound 5 (24 mg, 38.7 μmol) and anhydrous $K_2CO_3$ (10.7 mg, 77.5 μmol) in methanol (5 mL) was stirred vigorously at room temperature until the disappearance of compound 5. The solvent was removed under vacuum, and the residue was partitioned between water (10 mL) and $CH_2Cl_2$ (10 mL). The aqueous phase was extracted with $CH_2Cl_2$ (2×10 mL), and the combined organic phase was dried over $Na_2SO_4$ and evaporated to dryness. After purification by chromatography on silica gel (elution with hexane/ethyl acetate, 3:1), compound 6 (19 mg, 87%) was obtained.

Example 7

Synthesis of 3β-acetoxy-23-(4,4-difluoro-1,3,5,7-tetramethyl-4-bora-3a,4a-diaza-s-indacene-8-yl)-24-nor-5β-cholestane (Compound 7)

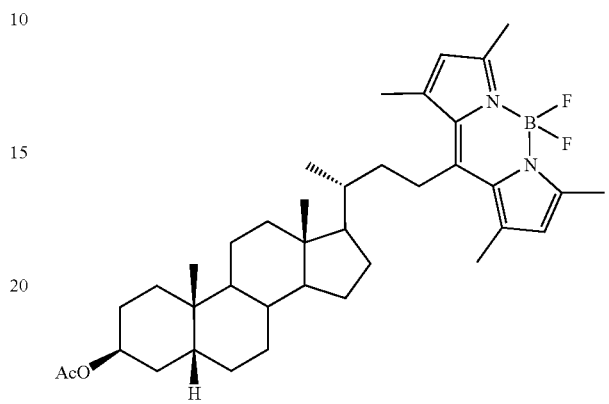

Compound 7 was prepared in 28% yield from 3β-acetoxy-5β-cholestan-24-oic acid according to the method described for compound 5.

Example 8

Synthesis of 23-(4,4-difluoro-1,3,5,7-tetramethyl-4-bora-3a,4a-diaza-s-indacen-8-yl)-24-nor-5β-cholestan-3β-ol (Compound 8)

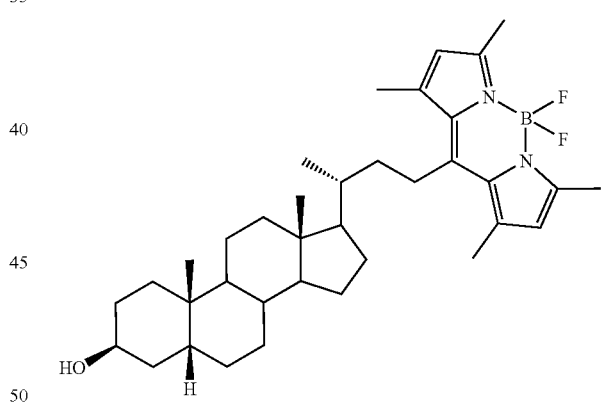

The same method used to prepare compound 6 was used to prepare compound 8 from compound 7, with a yield of 72%.

Example 9

Synthesis of Compound 9

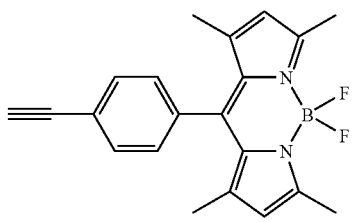

To a solution of p-ethynylbenzaldehyde (0.13 g, 1 mmol) and 2,4-dimethylpyrrole (0.22 g, 2.3 mmol) in CH$_2$Cl$_2$ (50 mL) was added trifluoroacetic acid (7.6 μL, 0.1 mmol) under nitrogen. After the mixture was stirred at room temperature overnight, a solution of p-chloranil (0.25 g, 1 mmol) in CH$_2$Cl$_2$ (5 mL) was added. The mixture was stirred at room temperature for 30 min. After BF$_3$.OEt$_2$ and Et$_3$N were added, the mixture was stirred further at room temperature for 6 h. The mixture was washed with water (3×20 mL) and dried over anhydrous Na$_2$SO$_4$. The solvent was removed and the residue was purified by chromatography on silica gel (elution with hexane/ethyl acetate, 10:1) to give 99 mg (28%) compound 9 as a dark solid.

Example 10

Synthesis of 22-azido-3β-tetrahydropyranyloxy-23-bisnorchol-5-en (compound 10)

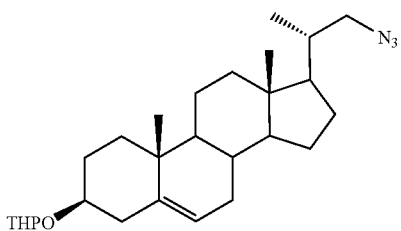

To a solution of compound 1 (2.4 g, 5.7 mmol) and Et$_3$N (5.8 g, 57.6 mmol) in CH$_2$Cl$_2$ (150 mL) was added methanesulfonyl chloride (3.3 g, 28.8 mmol) dropwise at 0° C. After being stirred at room temperature for 3 h, the mixture was washed with water (3×100 mL) and dried over anhydrous Na$_2$SO$_4$. The solvent was removed to give the mesylate quantitatively. A solution of the mesylate and lithium bromide (0.99 g, 11.7 mmol) in THF (100 mL) was heated at reflux for 24 h. The solvent was removed and the residue was dissolved in CH$_2$Cl$_2$ (100 mL). The solution was washed with water (3×100 mL) and dried over anhydrous Na$_2$SO$_4$. The solvent was removed under vacuum to give the corresponding bromide (2.7 g, 98%) as a white solid. The bromide (0.30 g, 0.63 mmol), sodium azide (0.12 g, 1.88 mmol), and lithium iodide (10 mg, 0.075 mmol) were dissolved in dry N,N-dimethylformamide (DMF) (10 mL). After the mixture was stirred at 80° C. for 18 h under vigorous stirring, it was cooled to room temperature, and water (20 mL) was added. The white particulate was collected by filtration and washed several times with water, and dried under vacuum to give crude compound 10 as a white solid. Pure compound 10 (0.235 g, 85%) was obtained by chromatography.

Example 11

Synthesis of Compound 11

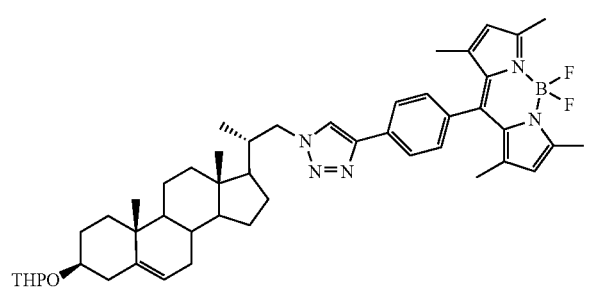

A mixture of compound 9 (16.8 mg, 48 μmol), compound 10 (21.3 mg, 48 μmol), and cuprous iodide (0.9 mg, 4.8 μmol) in dimethylsulfoxide (DMSO) (3 mL) was heated at 80° C. for 5 h. After the mixture was cooled to room temperature, water (10 mL) was added. The mixture was extracted with diethyl ether (4×20 mL), and the combined ether solutions were washed with water (2×20 mL) and dried over Na$_2$SO$_4$. The solvent was removed under vacuum, and the residue was purified by chromatography on silica gel (elution with hexane/ethyl acetate, 10:1) to give compound 11 (22.4 mg, 59%) as a red solid.

Example 12

Synthesis of Compound 12

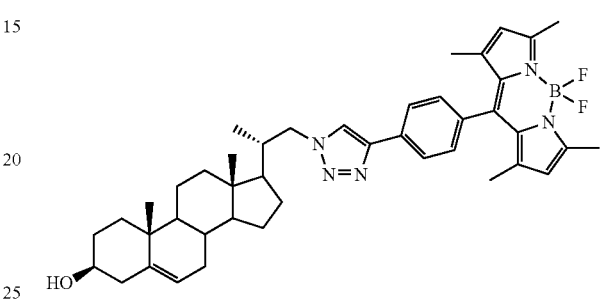

Compound 12 was prepared by the same method described for compound 6.

Example 13

Synthesis of 2-[2-(4'-bromophenyl)]vinyl-1H-pyrrole (compound 13)

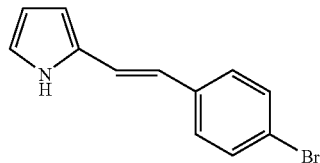

To a solution of 1H-pyrrole-2-carboxaldehyde (0.95 g, 10 mmol) and (4-bromobenzyl)phosphonic acid diethyl ester (3.69 g, 12 mmol) in dry THF (20 mL), was added potassium tert-butoxide (3.37 g, 30 mmol) at 0° C. with vigorous stirring. The mixture was stirred at 0° C. for 1 h and then allowed to warm to room temperature. After the mixture was stirred at room temperature for 1 day, water (20 mL) was added. The mixture was extracted with CH$_2$Cl$_2$ (3×50 mL), and the combined organic solution was washed with water (2×50 mL), and then dried over anhydrous Na$_2$SO$_4$. The solvent was removed under vacuum and the residue was purified by chromatography on silica gel (elution with hexane/ethyl acetate, 10:1) to give compound 13 (1.72 g, 69%) as a blue solid.

Example 14

Synthesis of 2-[2-(4'-trimethylsilylethynylphenyl)]vinyl-1H-pyrrole (compound 14)

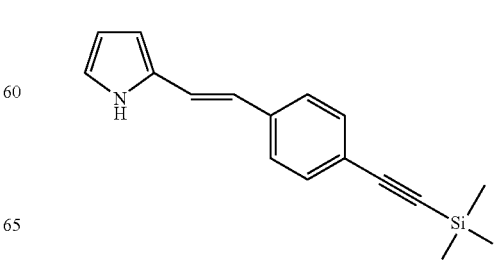

To a solution of compound 13 (0.5 g, 2.0 mmol), trimethylsilylacetylene (0.98 g, 10.0 mmol), and diisopropylethylamine (4 mL) in THF (12 mL) were added cuprous iodide (58 mg, 0.30 mmol) and tetrakis(triphenylphosphorus)palladium (0.36 g, 0.3 mmol) under nitrogen. The resulting mixture was stirred at room temperature until the disappearance of compound 13 was noted by TLC. Water (10 mL) was added and the mixture was extracted with $CH_2Cl_2$ (3×30 mL). The combined $CH_2Cl_2$ solution was dried over $Na_2SO_4$. The solvent was removed and the resulting mixture was purified by chromatography on silica gel (elution with hexane/ethyl acetate, 10:1) to give compound 14 (0.30 g, 56%).

Example 15

Synthesis of Compound 15

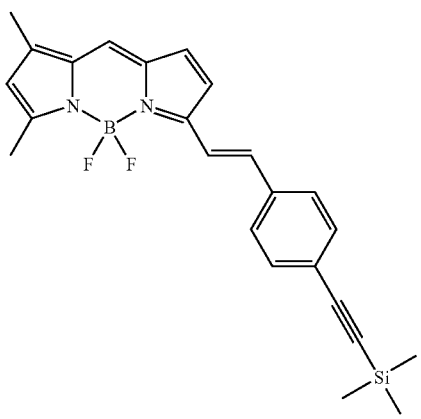

To a solution of compound 14 (0.36 g, 1.35 mmol) and 3,5-dimethyl-pyrrole-2-carboxaldehyde (0.17 g, 1.35 mmol) in $CH_2Cl_2$ (20 mL) was added phosphorus oxychloride (0.21 g, 1.35 mmol). The mixture was stirred at room temperature overnight before $BF_3.OEt_2$ (0.70 mL, 5.40 mmol) and $Et_3N$ (0.95 mL, 5.40 mmol) were added. The mixture was stirred for 6 h at room temperature, washed with water (3×10 mL), and dried over $Na_2SO_4$. After the solvent was removed under vacuum, the residue was purified by chromatography on silica gel (elution with a gradient of hexane/ethyl acetate, 10:1 to 6:1) to give compound 15 (0.29 g, 51%) as a blue solid.

Example 16

Synthesis of Compound 16

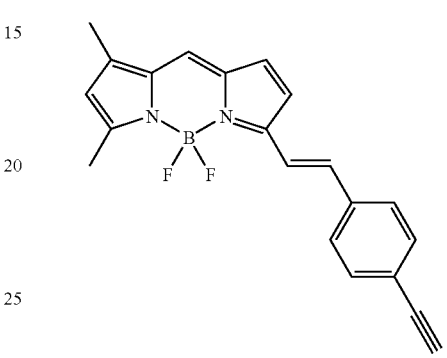

To a solution of compound 15 (42 mg, 0.1 mmol) in methanol (3 mL) and $CH_2Cl_2$ (1 mL) was added potassium carbonate (41 mg, 0.3 mmol). The mixture was stirred at room temperature until the disappearance of compound 15 was noted by thin-layer chromatography (TLC). Acetic acid (0.1 mL) was added, and the mixture was stirred at room temperature for 30 min. The solvent was removed under vacuum, and the resulting solid was dissolved in $CH_2Cl_2$ (20 mL). The solution was washed with water (3×10 mL) and dried over anhydrous $Na_2SO_4$. The solvent was removed under vacuum and the residue was purified by chromatography on silica gel (elution with hexane/ethyl acetate, 10:1) to give compound 16 (22.1 mg, 64%) as a blue solid.

Example 17

Synthesis of Compound 17

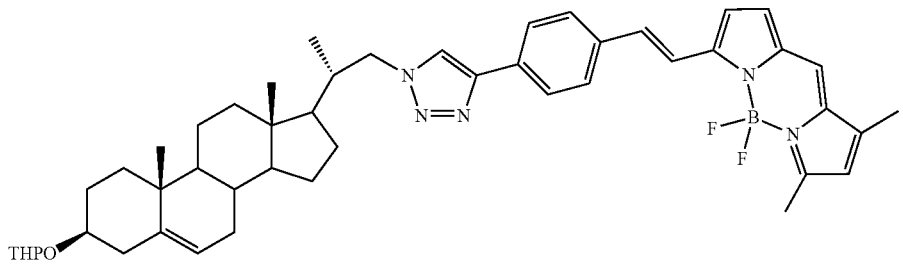

Compound 17 was synthesized from compound 10 and compound 16 by the method described above for compound 11.

Example 18

Synthesis of Compound 18

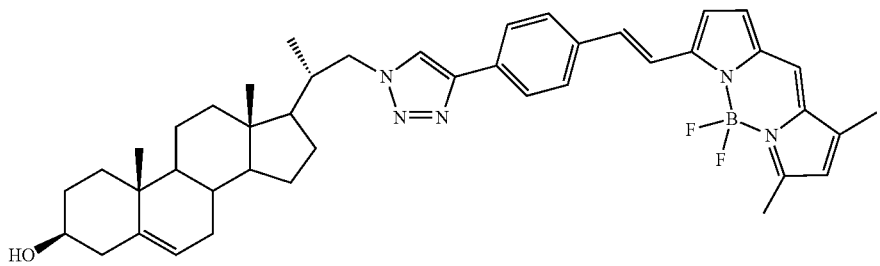

Compound 18 was prepared from compound 17 by the same method described above for compound 6.

Example 19

Synthesis of Compound 19

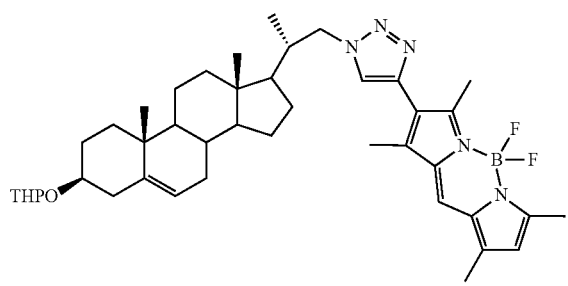

Compound 19 is prepared from compound 10 and compound 20 (structure P wherein X=—C≡CH) by the method described above for compound 11.

Example 20

Synthesis of Compound 21

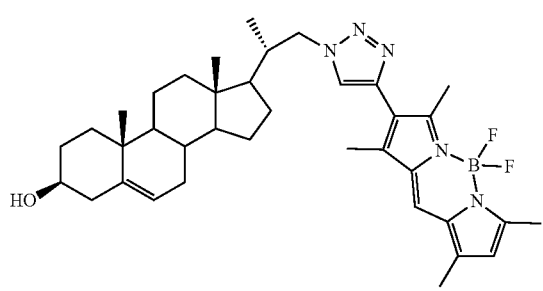

Compound 21 is prepared form compound 19 by the same method described above for compound 6.

Example 21

Synthesis of Compound 22

22

To a stirred solution of compound 6 (24 mg, 0.050 mmol) and triphenylphospine (14 mg, 0.050 mmol) in dichloromethane (2 mL) was added diisopropyl azodicarboxylate (11 mg, 0.050 mmol) at −23° C. under $N_2$. After the mixture was stirred at −23° C. for 1 hour, the reaction mixture was warmed to 0° C. and chloroacetic acid (5 mg, 0.050 mmol) was added. The mixture was stirred at room temperature overnight, the solvent was removed under vacuum, and the residue was purified by flash chromatography to give compound 22 (6.9 mg, 21%).

Example 22

Synthesis of Compound 23

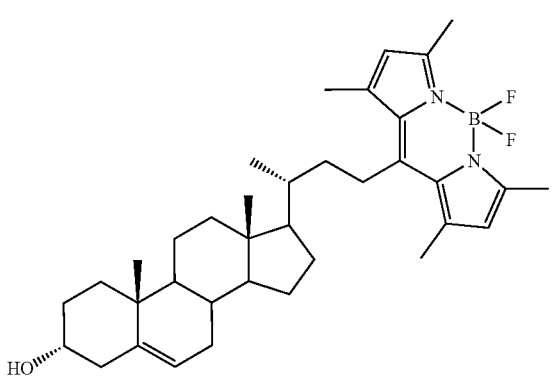

To a solution of compound 22 (6.9 mg, 0.010 mmol) in methanol (3 mL) was added potassium carbonate (5.5 mg, 0.040 mmol). The mixture was stirred at room temperature until the disappearance of compound 22, as monitored by thin-layer chromatography. The solvent was removed under vacuum, and the residue was distributed in dichloromethane (5 mL) and water (5 mL). The aqueous layer was extracted twice with dichloromethane, and the combined dichloromethane layer was dried with anhydrous $Na_2SO_4$, and concentrated. The crude product was purified by flash chromatography to give compound 23 (4.6 mg, 80%) as a dark solid.

We claim:

1. A molecule having formula I, II, or III,

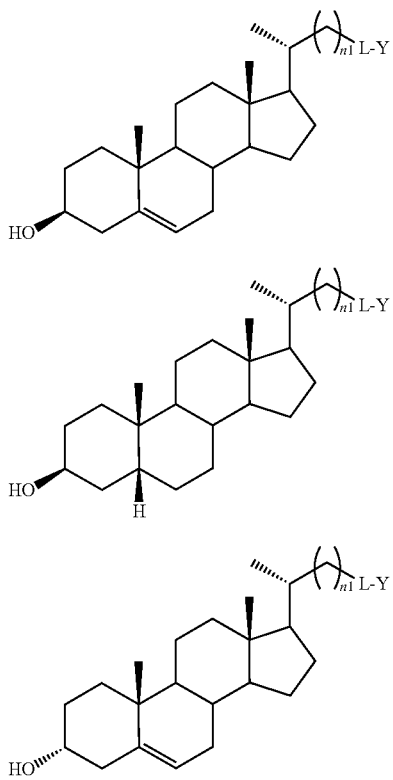

wherein:
L represents a linker having one of the following structures:

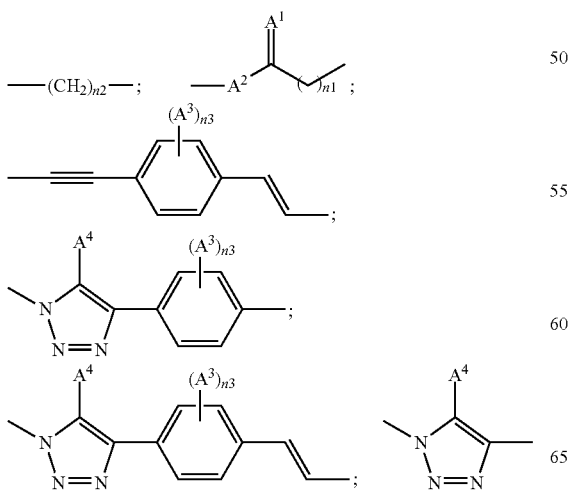

Y represents the following formula:

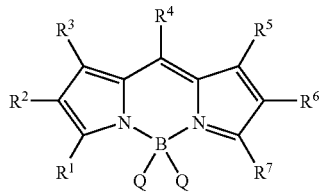

wherein:
n1 is independently 1, 2, 3, 4, or 5;
n2 is 0, 1, 2, 3, or 4;
n3 is independently 0, 1, 2, 3, or 4;
$A^1$ is O, S or $H_2$;
$A^2$ is O, S, or NH;
$A^3$ is independently alkyl, aryl, alkoxy, or aryloxy;
$A^4$ is independently hydrogen, alkyl, or aryl;
$R^1$, $R^2$, $R^3$, $R^4$, $R^5$, $R^6$, and $R^7$ independently represent hydrogen, alkyl, phenyl, alkoxy, or carboalkoxy; or $R^1$ and $R^2$, $R^2$ and $R^3$, $R^5$ and $R^6$, or $R^6$ and $R^7$ represent benzo provided that one of $R^1$ through $R^7$ represents a bond to L;
Q is fluoro, alkyl, alkoxy, or aryloxy;
alkyl groups are unbranched, saturated, and have 1-4 carbon atoms;
aryl groups can be either carbocyclic aryl or heterocyclic aryl;
carbocyclic aryl groups have a total of 6-20 carbon atoms, including carbon atoms of substituents;
heterocyclic aryl groups have a total of 5-20 carbon atoms, including carbon atoms of substituents;
alkoxy groups are alkyloxy groups wherein alkyl groups are as defined above;
the aryl groups of aryloxy are as described above;
carboalkoxy groups are alkyl esters of a carboxylic acid wherein alkyl groups are as defined above;
each alkyl, aryl, alkoxy, aryloxy, benzo, and carboalkoxy, independently, may be unsubstituted or substituted with one or more substituent;
alkyl substituents are halo, hydroxyl, amino, or aryl;
aryl substituents are halo, hydroxyl, amino, alkyl, aryl, nitro, or carboxyl; and
halo substituents are fluoro or chloro.

2. A molecule according to claim 1, having formula I or II.

3. A molecule according to claim 1, wherein:
n1 is independently 1 or 2;
n2 is 0 or 1;
n3 is 0;
$A^1$ is O;
$A^2$ is O;
$A^4$ is hydrogen;
Q is fluoro;
$R^1$, $R^2$, $R^3$, $R^4$, $R^5$, $R^6$, and $R^7$ independently represent hydrogen or alkyl;
alkyl groups are methyl and ethyl; and
aryl groups are phenyl.

4. A molecule according to claim 1, having formula I or II wherein:
L represents

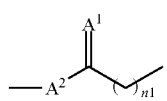

$R^4$ represents a bond to L; and
Q is fluoro.

5. A molecule according to claim 4, having formula I.
6. A molecule according to claim 1, having formula I or II wherein:
L represents —(CH$_2$)$_{n2}$— n2 is 0;
R$^4$ represents a bond to L; and
Q is fluoro.
7. A molecule according to claim 6, having formula I.
8. A molecule according to claim 1, having formula I or II wherein:
L represents

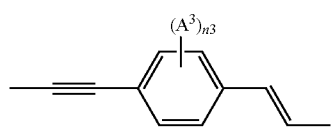

n3 is 0;
R$^1$ represents a bond to L; and
Q is fluoro.
9. A molecule according to claim 8, having formula I.
10. A molecule according to claim 1, having formula I or II wherein:
L represents

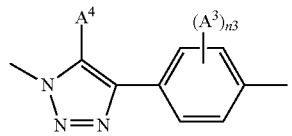

A$^4$ is hydrogen;
n3 is 0;
R$^4$ represents a bond to L; and
Q is fluoro.
11. A molecule according to claim 10, having formula I.
12. A molecule according to claim 1 having formula I or II wherein:
L represents

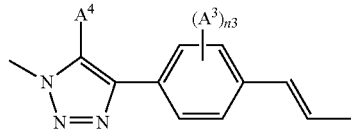

A$^4$ is hydrogen;
n3 is 0;
R$^1$ represents a bond to L; and
Q is fluoro.
13. A molecule according to claim 12, having formula I.
14. A molecule according to claim 1, having formula II wherein:
L represents —(CH$_2$)$_{n2}$— n2 is 0;
R$^4$ represents a bond to L; and
Q is fluoro.
15. A molecule according to claim 1, having formula I or II wherein:
L represents

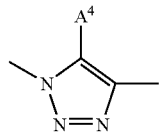

A$^4$ is hydrogen;
R$^2$ represents a bond to L; and
Q is fluoro.
16. A molecule according to claim 15, having formula I.

* * * * *